United States Patent
Gupta (10) Patent No.: US 10,908,270 B2
(45) Date of Patent: Feb. 2, 2021

(54) PORTABLE ULTRASOUND IMAGING SYSTEM WITH ACTIVE COOLING

(71) Applicant: FUJIFILM SonoSite, Inc., Bothell, WA (US)

(72) Inventor: Rahul Gupta, Bothell, WA (US)

(73) Assignee: FUJIFILM SONOSITE, INC., Bothell, WA (US)

(*) Notice: Subject to any disclaimer, the term of this patent is extended or adjusted under 35 U.S.C. 154(b) by 0 days.

(21) Appl. No.: 15/874,507

(22) Filed: Jan. 18, 2018

(65) Prior Publication Data
US 2019/0219677 A1 Jul. 18, 2019

(51) Int. Cl.
*H05K 7/20* (2006.01)
*G01S 7/52* (2006.01)
*A61B 8/00* (2006.01)

(52) U.S. Cl.
CPC ........ *G01S 7/52079* (2013.01); *A61B 8/4272* (2013.01); *A61B 8/4427* (2013.01); *A61B 8/4461* (2013.01); *A61B 8/461* (2013.01); *A61B 8/546* (2013.01); *G01S 7/52053* (2013.01)

(58) Field of Classification Search
CPC ............. G01S 7/52079; G01S 7/52053; A61B 8/4427; A61B 8/461
See application file for complete search history.

(56) References Cited

U.S. PATENT DOCUMENTS

| | | | | | |
|---|---|---|---|---|---|
| 5,689,403 | A | * | 11/1997 | Robertson, Jr. ........ | H04B 1/036 361/695 |
| 6,046,921 | A | * | 4/2000 | Tracewell ............... | H02M 3/00 361/696 |
| 6,542,846 | B1 | * | 4/2003 | Miller .................... | A61B 8/546 340/584 |
| 9,186,123 | B1 | * | 11/2015 | Dunham .................. | A61B 8/00 |
| 9,801,613 | B2 | * | 10/2017 | Mander .................. | A61B 8/463 |
| 2002/0122296 | A1 | * | 9/2002 | Stone ...................... | G06F 1/184 361/679.48 |
| 2004/0135482 | A1 | * | 7/2004 | Thielemans .......... | H01L 51/529 313/22 |
| 2008/0002356 | A1 | * | 1/2008 | Kwong ................... | G06F 1/203 361/679.48 |
| 2008/0239245 | A1 | * | 10/2008 | Kitahara .................. | A61B 8/12 353/61 |
| 2010/0014250 | A1 | * | 1/2010 | Kitahara .................. | A61B 8/12 361/695 |
| 2011/0058326 | A1 | * | 3/2011 | Idems ...................... | G09F 9/30 361/679.21 |

(Continued)

*Primary Examiner* — Binh B Tran
*Assistant Examiner* — Michael A Matey
(74) *Attorney, Agent, or Firm* — Womble Bond Dickinson (US) LLP (57) ABSTRACT

An ultrasound imaging system includes a thermally conductive frame and a number of electronic components and a display that are sealed within the frame. The frame further includes a plenum extending through the frame with surfaces that are thermally coupled to the electronic components and the display. An active cooling mechanism, such as one or more fans, moves air through the plenum to remove heat generated by the electronic components and display. The plenum is environmentally sealed so that moisture, dust, air or other contaminants drawn into the plenum do not contact the sealed electronic components and display in the frame.

20 Claims, 8 Drawing Sheets

(56) References Cited

U.S. PATENT DOCUMENTS

| | | | |
|---|---|---|---|
| 2011/0276113 A1* | 11/2011 | Cybulski | A61B 18/1482 |
| | | | 607/101 |
| 2014/0206412 A1* | 7/2014 | DeJohn | G01N 21/77 |
| | | | 455/556.1 |
| 2015/0029658 A1* | 1/2015 | Yairi | H05K 1/0212 |
| | | | 361/679.47 |
| 2015/0351727 A1* | 12/2015 | Nieminen | A61B 8/4455 |
| | | | 600/459 |
| 2016/0007957 A1* | 1/2016 | Murphy | H01R 13/6315 |
| | | | 600/459 |
| 2016/0007965 A1* | 1/2016 | Murphy | G01S 7/52084 |
| | | | 345/173 |
| 2016/0041423 A1* | 2/2016 | Dunn | H05K 7/20154 |
| | | | 362/97.3 |
| 2016/0048365 A1* | 2/2016 | Henderson | G06F 3/1423 |
| | | | 345/473 |
| 2016/0242747 A1* | 8/2016 | Siedenburg | A61B 8/546 |
| 2016/0286694 A1* | 9/2016 | Krishnan | H05K 7/20772 |
| 2016/0324040 A1* | 11/2016 | Bouissiere | H05K 7/20972 |
| 2017/0043189 A1* | 2/2017 | Stoddard | A61B 8/4281 |
| 2017/0056686 A1* | 3/2017 | Gamelin | H01L 25/0753 |
| 2017/0065259 A1* | 3/2017 | Pinch | A61B 8/546 |
| 2018/0132380 A1* | 5/2018 | Baran | H05K 7/1465 |
| 2019/0320555 A1* | 10/2019 | Flavin | H05K 5/069 |
| 2019/0365350 A1* | 12/2019 | Chiang | A61B 8/4427 |

* cited by examiner

PORTABLE ULTRASOUND IMAGING SYSTEM WITH ACTIVE COOLING

TECHNICAL FIELD

The disclosed technology relates generally to ultrasound imaging systems and in particular to portable ultrasound imaging systems.

BACKGROUND

As will be appreciated by those skilled in the art, most modern ultrasound imaging systems work by creating acoustic signals from a transducer having a number of individual transducer elements that are formed in a sheet of piezoelectric material. By applying a voltage pulse across an element, the element is physically deformed thereby causing a corresponding ultrasound signal to be generated. The signal travels into a region of interest where a portion of the signal is reflected back to the transducer as an echo signal. When an echo signal impinges upon a transducer element, the element is vibrated causing a change in the voltage across the element that is detected as an electronic signal. Electronic signals from multiple transducer elements are combined and analyzed to determine characteristics of the combined signal such as its amplitude, frequency, phase shift, power and the like. The characteristics are quantified and converted into pixel data that is used to create an image of the region of interest.

As the processing power of integrated circuits has steadily increased, the sizes of electronic devices have correspondingly decreased. Ultrasound imaging systems are now being sold in form factors as small as hand-held smart phones and tablet computers. While the size of the devices is convenient, there is less room to dissipate the heat generated by the electronics. The processing power required to provide a full featured ultrasound imaging system generates a significant amount of heat. There are federal guidelines for how hot a consumer medical device can get during use. While various methods have been proposed to reduce the heating, improvements can be made.

SUMMARY

To address these and other concerns, the technology disclosed herein is directed to a portable ultrasound imaging system with built-in active cooling to remove heat that is generated by the electronic components during use. In the disclosed embodiments, the ultrasound imaging system is built on a thermally conductive frame having a sealed interior plenum with an input port and one or more output ports. Electronic components of the imaging system are thermally coupled to the outer surfaces of the plenum and a fan moves air through the interior of the plenum between the input port and the one or more output ports.

In some embodiments, one or more of the interior surfaces of the plenum include cooling fins to aid in dissipating heat from the electronic components. The plenum is environmentally sealed so that liquids and dust that enter the plenum are prevented from coming into contact with the electronic components.

DETAILED DESCRIPTION

Figure 1:
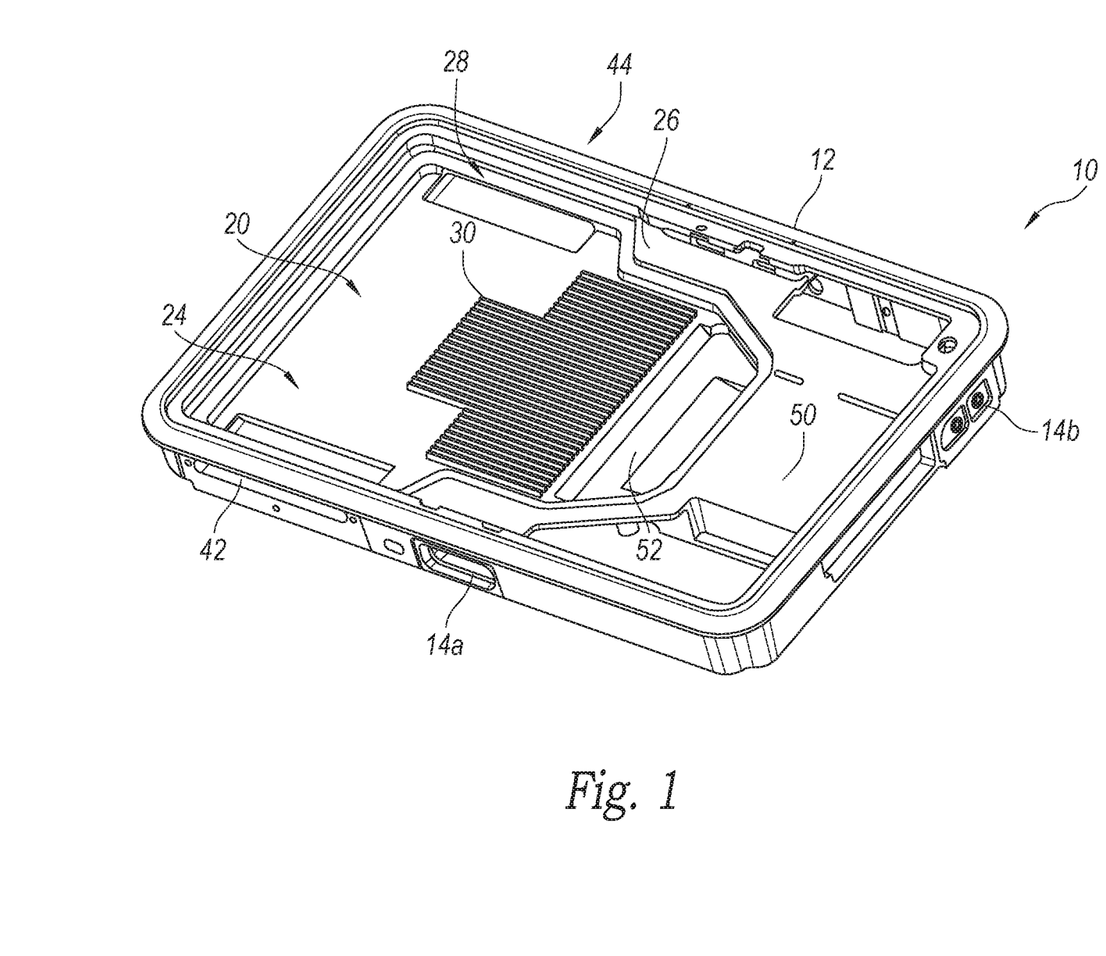
FIG. 1 illustrates a top isometric view of a thermally conductive frame in accordance with an embodiment of the disclosed technology.

As indicated above, one of the problems with ultra-portable ultrasound imaging systems is being able to dissipate the heat that is generated by the electronic components when the system is operating. To address this issue, one embodiment of the disclosed technology utilizes a thermally conductive frame as shown in FIG. 1 to support the electronics and a display screen. The thermally conductive frame 10 is preferably machined or cast from a thermally conductive material such as a metal (e.g. aluminum or copper etc.) but could also be made from a thermally conductive plastic material such as CoolPoly® materials made by the Celanese Corp.

In one embodiment, the thermally conductive frame 10 is generally rectangular in shape with an outer rim 12 surrounding its perimeter. The outer rim 12 includes a number of apertures 14*a*, 14*b*, 14*c* that extend through the rim and align with various electrical connectors and controls in imaging system (e.g. USB port, audio port, power connection port, ultrasound imaging probe port, on/off switch, volume controls etc.).

The thermally conductive frame has a plenum 20 in the interior of the conductive frame that is defined as a space or gap between a lower portion 24 and an upper portion 26 in the frame 10. The purpose of the plenum is to keep outside air, dust and water or other contaminants from coming in contact with the electronics and hence keep the unit environmentally sealed/ingress protected. In the embodiment shown, the upper portion 26 has a recessed lip 28 extending around a perimeter of the top of the plenum on the interior of the rim 12. The lip 28 is configured to receive a cover (shown in FIG. 3) that operates to seal the plenum 20 so that liquids, dust or other contaminants within the plenum cannot migrate from within the plenum into the remaining areas of the frame 10. In one embodiment, the plenum 20 is made without the cover in place so that the conductive frame 10 can be molded or machined. In some embodiments, one or more interior surfaces of the plenum have a number of cooling fins 30 or other heat dissipating structures that increase the surface area over which cooling air passes and therefore facilitates heat transfer. In some embodiments, the cooling fins 30 may be aligned with electrical components drawing the highest amounts of power.

In the embodiment shown, the rim 12 of the conductive frame 10 includes a number of apertures that open into the interior of the plenum. A pair of ports 42, 44 on opposite sides of the rim 12 define output ports of the plenum that vent air that is moved through the plenum as will be described below.

Figure 2:
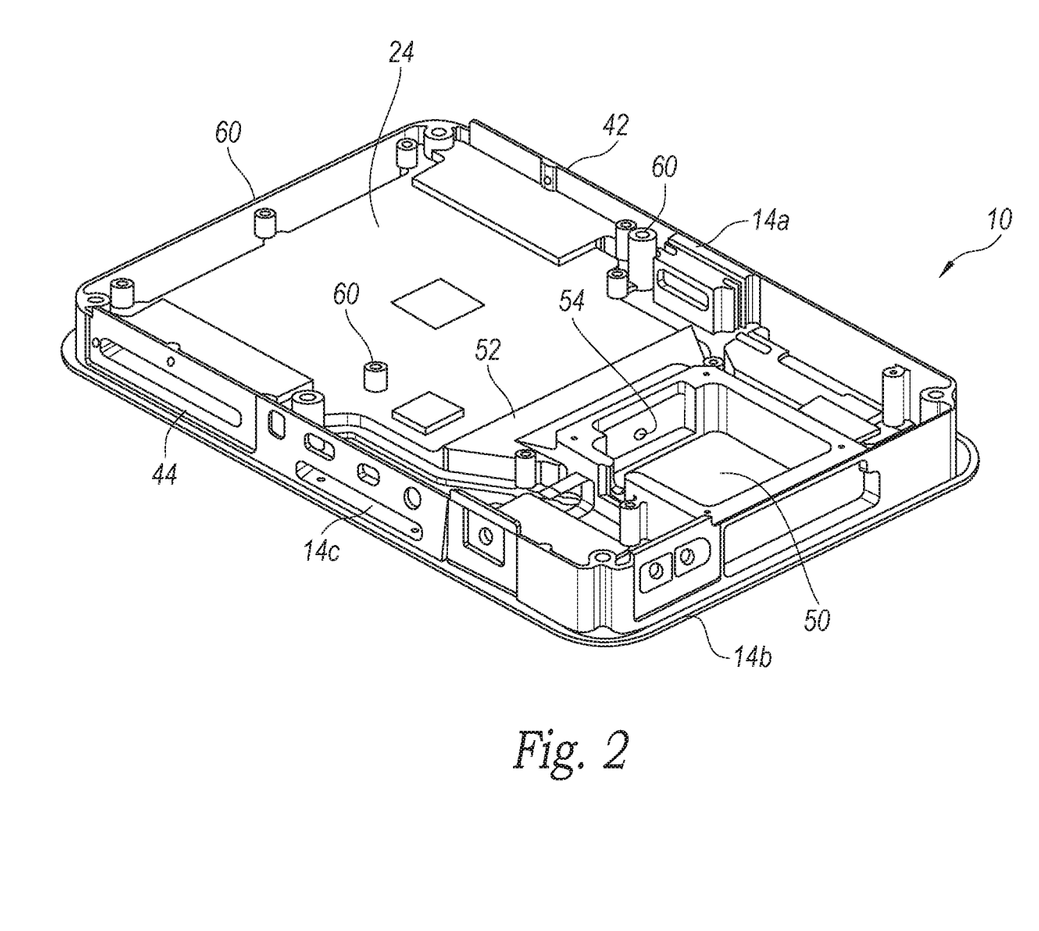
FIG. 2 illustrates a bottom isometric view of the thermally conductive frame in accordance with an embodiment of the disclosed technology.

As best shown in FIG. 2, the frame 10 has a pocket 50 formed therein that receives an active cooling mechanism such as a horizontally spinning fan (blower fan) (not shown). In some embodiments, the active cooling mechanism can be ingress protected. For example, a DC brushless blower type fan no. BFB0405HHA-TZP4 from Delta Electronics of Thailand has an ingress protection rating of IP55. In some embodiments, the ingress protection rating of the active cooling mechanism exceeds the ingress protection rating of the overall ultrasound system. In other embodiments, the ingress protection rating of the active cooling mechanism is less than or equal to the ingress protection rating of the overall ultrasound system. In one embodiment, a funnel portion 52 directs air in a unilateral direction from an input port 54 towards the output ports 42,44 of the plenum. When the fan is in the pocket 50 and is operated, air is moved through the input port 54 into the funnel portion 52 and into the distal area of the plenum. In another embodiment, the funnel portion 52 directs air in the other direction from the pair of ports 42, 44 towards the port 54. It is generally desirable to position the electronic components that draw the most power near the location where cool air is drawn into the plenum to increase the cooling effect. Therefore, the direction of airflow is largely determined by where these components are placed in the frame 10. A number of cylindrical projections 60 are molded into the frame 10 to form bosses for securing a printed circuit board (not shown) to the underside of the thermally conductive frame 10 with fasteners such as machine screws.

Figure 3:
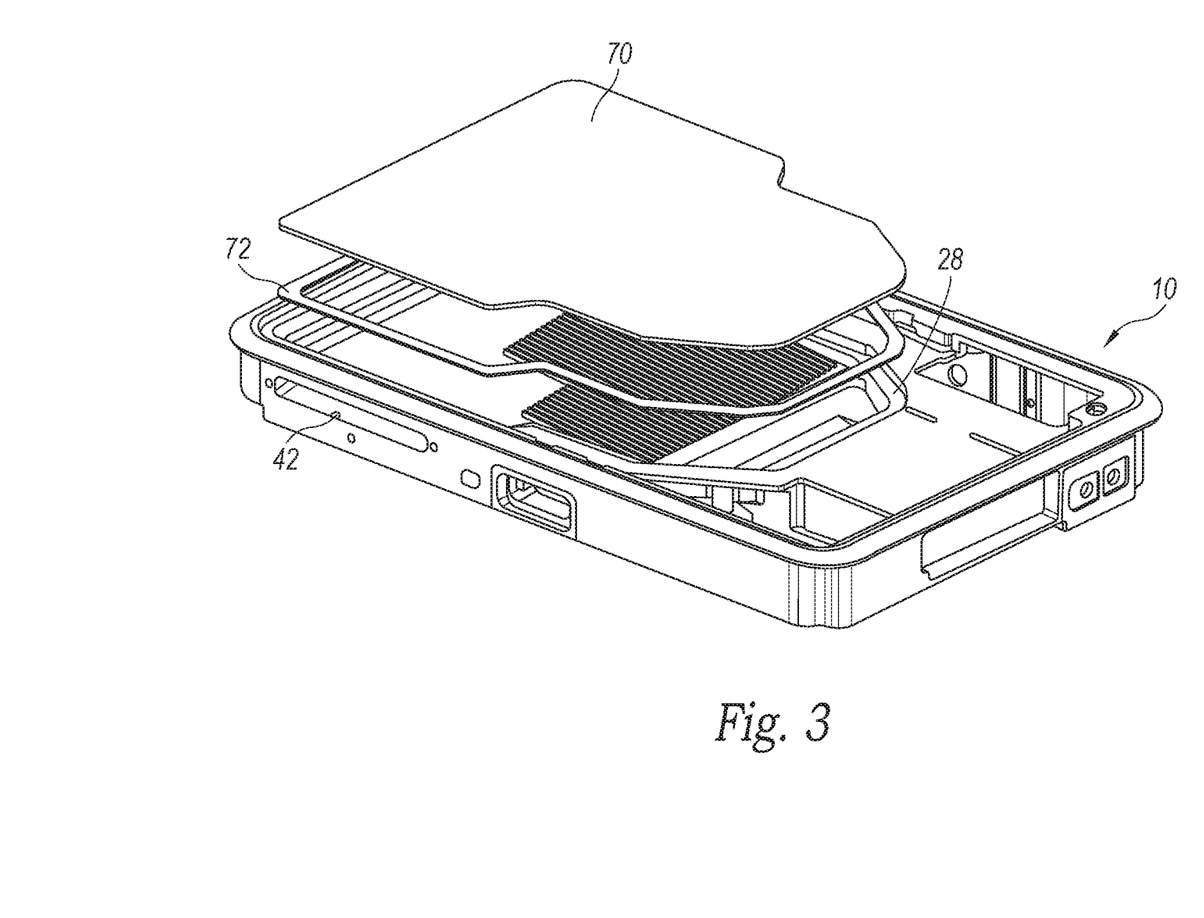
FIG. 3 illustrates a cover plate placed over an interior portion of the thermally conductive frame to define a plenum in accordance with an embodiment of the disclosed technology.

FIG. 3 illustrates how a cover 70 is secured in the recess 28 in the upper portion 26 of the plenum to seal the interior of the plenum. In some embodiments, the cover 70 is secured to the recess 28 with a water and dustproof seal 72 such as closed cell foam having an adhesive thereon in order to seal the interior of the plenum from the remainder of the frame. Liquids, dust or other contaminants in the plenum 20 cannot migrate though the seal 72 and into the other areas of the frame. In the embodiment shown, the plenum is necked down or has a smaller width in an area 74 (see FIG. 1) that is adjacent to the fan compared with the area of the plenum near the exhaust ports 42, 44. Air is moved faster in this necked down area 74 due to the reduced cross sectional area. In some embodiments, the interior surface (not shown) of the cover 70 includes cooling fins or other heat dissipating structures to increase the surface area of the cover and facilitate heat transfer through convection. In some embodiments, a relationship may exist where the distance from the input ports to the output ports ensures a minimum temperature drop of the system as the active cooling mechanism is operating. In further embodiments, there may be a temperature gradient from the necked area 74 of the plenum to the exhaust ports 42/44. The cover 70 is also made of a thermally conductive material such as aluminum so that heat generating components placed near the cover 70 or otherwise thermally connected to the cover 70 will transfer heat into the cover to be removed by air moving through the plenum.

Figure 4:
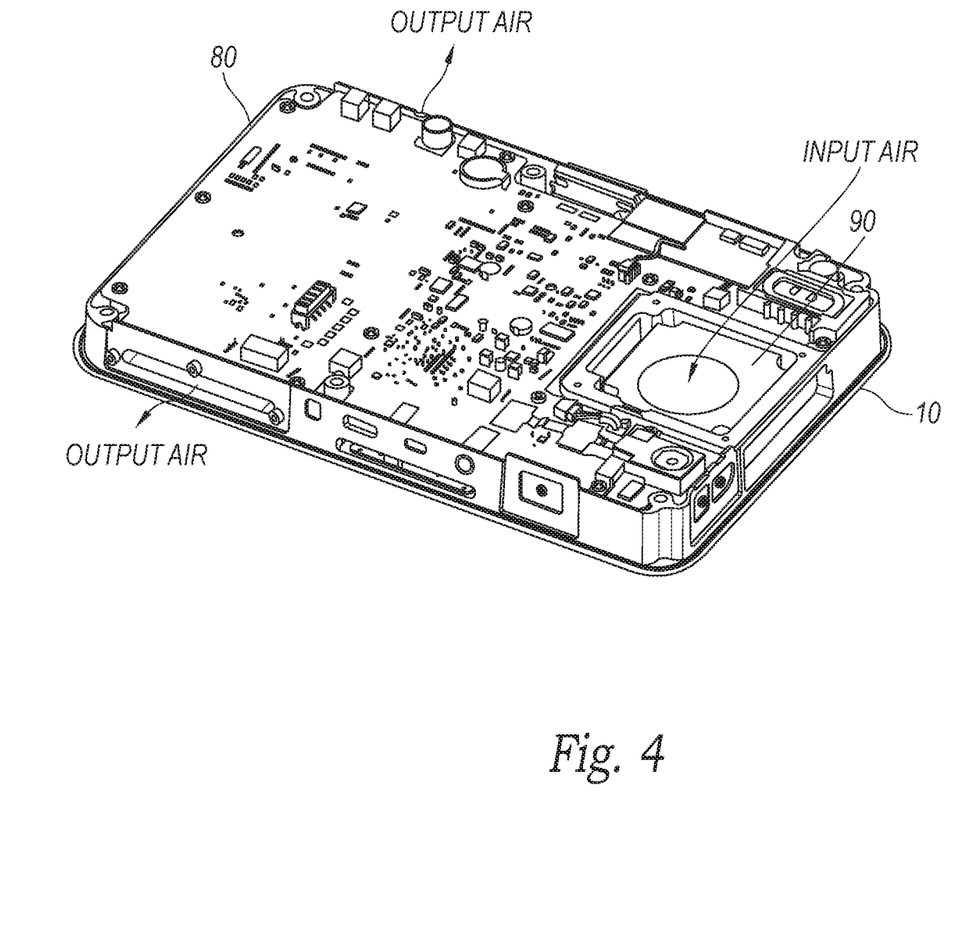
FIG. 4 illustrates a printed circuit board having one or more electronic components that are thermally coupled to an exterior surface of the plenum in the thermally conductive frame in accordance with an embodiment of the disclosed technology.

FIG. 4 shows a printed circuit board 80 that is mounted to the underside of the thermally conductive frame 10. The printed circuit board can be a single or double-sided circuit board having a number of electronic components mounted thereon (e.g. processors, DSPs, GPU's, CPU's, FPGA's, T/X-R/X ASICs, amplifiers, ND converters, voltage control circuits etc.) To remove the heat that is generated by these components, at least some of the components are thermally coupled directly or indirectly to the exterior surface portions of the plenum. Thermal coupling may be accomplished by placing the components adjacent to the exterior surface of the plenum or by placing a thermally conductive material (e.g. heat conductive pads, thermal grease) between the circuits the plenum.

In the view shown in FIG. 4, the underside of the frame 10 is shown facing up. Therefore, the electronic components on the top surface (not shown) of the printed circuit board 80 are thermally coupled to the bottom portion 24 or outer of the plenum. Heat from these circuits is absorbed into the thermally conductive bottom portion 24 and is removed by air that is moved by the fan 90 through the plenum. FIG. 4 shows one air path where air is drawn into the center area of a cooling fan 90 and is forced into the funnel area 52 (see FIG. 2) of the plenum before being expelled from the one or more exhaust ports 42, 44 on the sides of the frame 10.

Because the frame 10 is made of a thermally conductive material such as aluminum, it can absorb heat from other components from the ultrasound imaging system in addition to heat from those components that are directly adjacent to the top and bottom portions of the plenum. Heat transferred into the conductive frame 10 from these components can also be removed by the air that is moved by the fan 90. As will be appreciated, by having the sealed plenum 20 in the central portion of the frame 10, the plenum is able to remove heat that is generated by components that are positioned above and below the plenum. Components that generate more heat than others in the imaging system are preferably positioned near the necked down area 74 of the plenum that is close to the fan 90. This area of the plenum can provide the most heat transfer because the air that is moved by the fan 90 from the input port 54 to the exhaust ports 42/44 has a lower temperature as it enters the plenum and because it is moving faster due to the reduced cross sectional area of the plenum. In one embodiment, the electronic components placed in the necked down area 74 of the plenum draw approximately 4 watts or about ⅓ of the total power draw of the entire ultrasound imaging system. It is expected that with the thermally conductive frame 10 made of aluminum and the plenum configured as shown and described will operate in conjunction with a fan 90 that can move 3 cubic feet of air/minute to limit the maximum temperature rise of the ultrasound imaging system to 6-8 degrees C.

Figure 5:
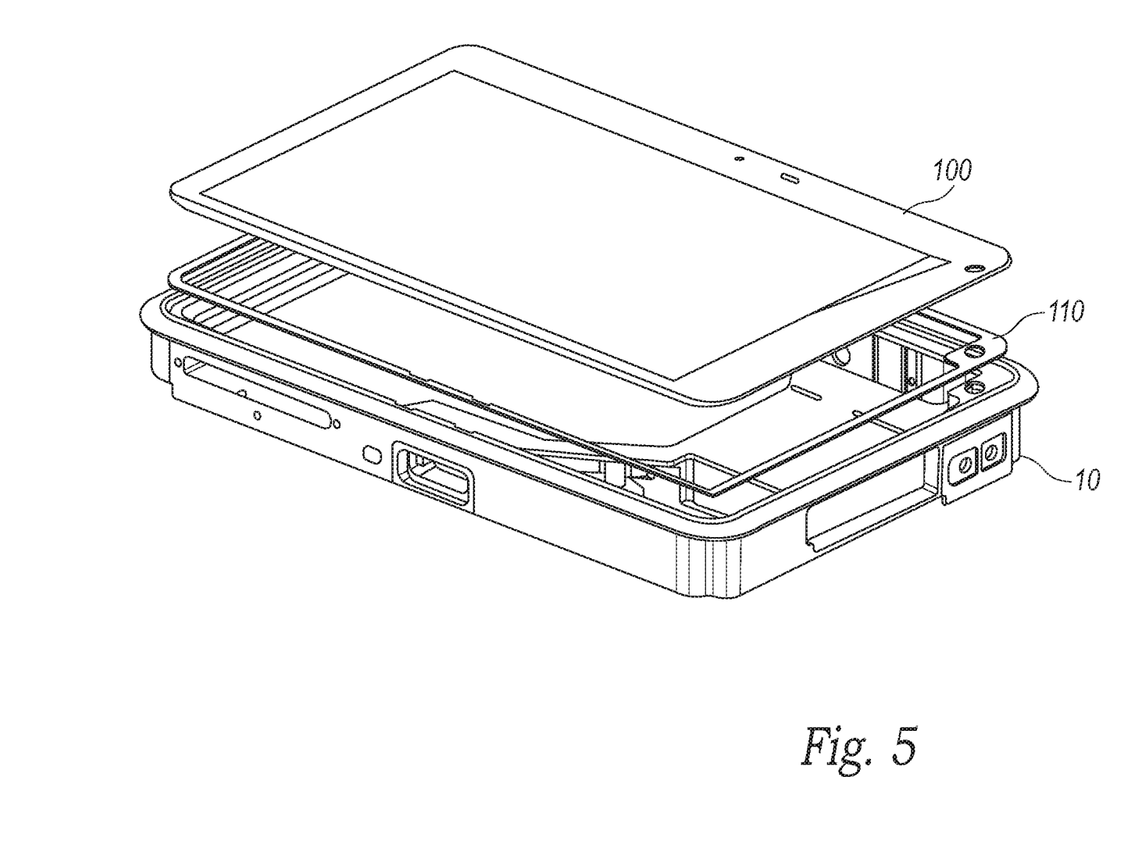
FIG. 5 illustrates how an electronic display screen is joined to the thermally conductive frame in accordance with an embodiment of the disclosed technology.
Figure 6:
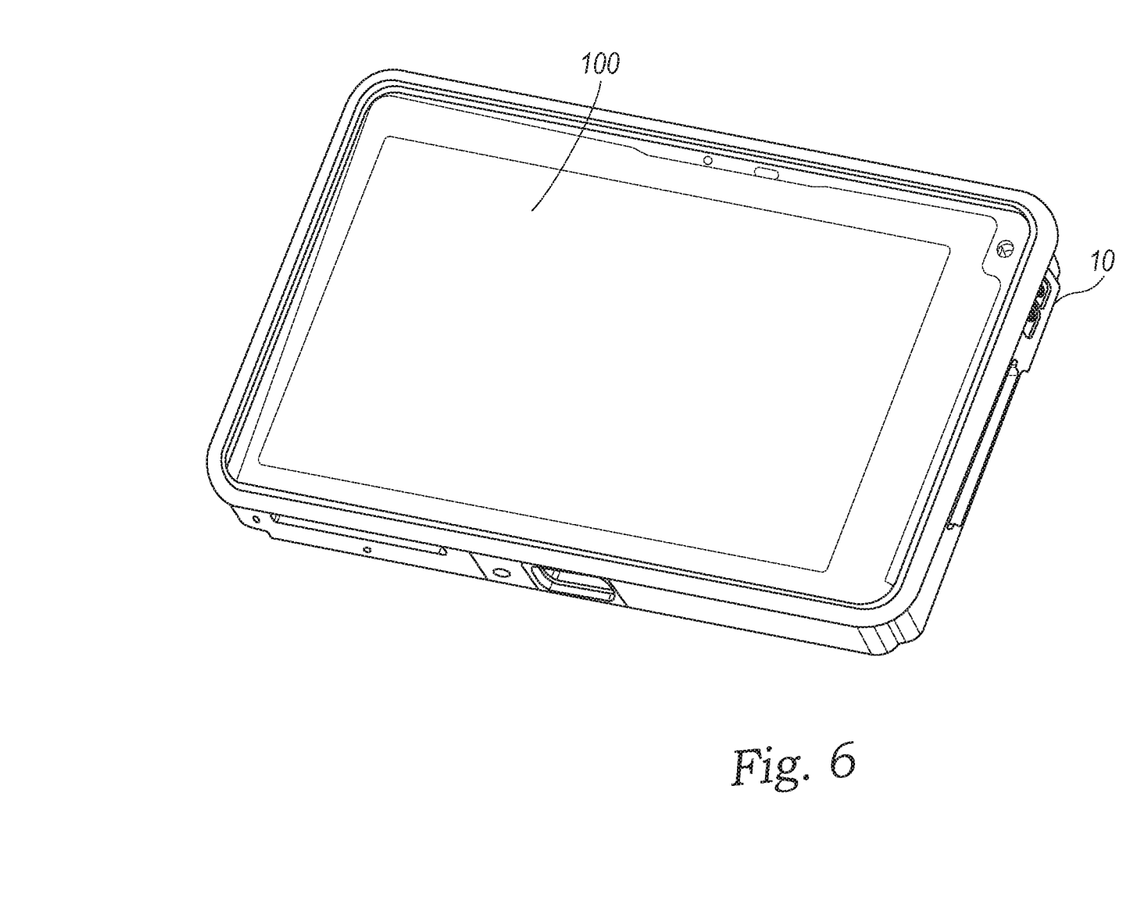
FIG. 6 shows the electronic display joined to the thermally conductive frame in accordance with an embodiment of the disclosed technology.

FIG. 5 shows a display screen 100 that is secured to the top of the thermally conductive frame 10. An adhesive gasket 110 is positioned between the display screen 100 and the frame to form a liquid/dust resistant seal and bond around the perimeter of the display screen. In one embodiment, the display screen comprises a touch sensitive, active LED color screen that generates heat during use. Heat from the screen 110 is transferred to the top portion 26 and cover 70 of the plenum and is removed by the air that is moved through the plenum by the fan 90. FIG. 6 shows the frame 10 with the display screen 100 in place. A bezel surrounding the rim of the frame 10 protects the edges of the display 100.

Figure 7:
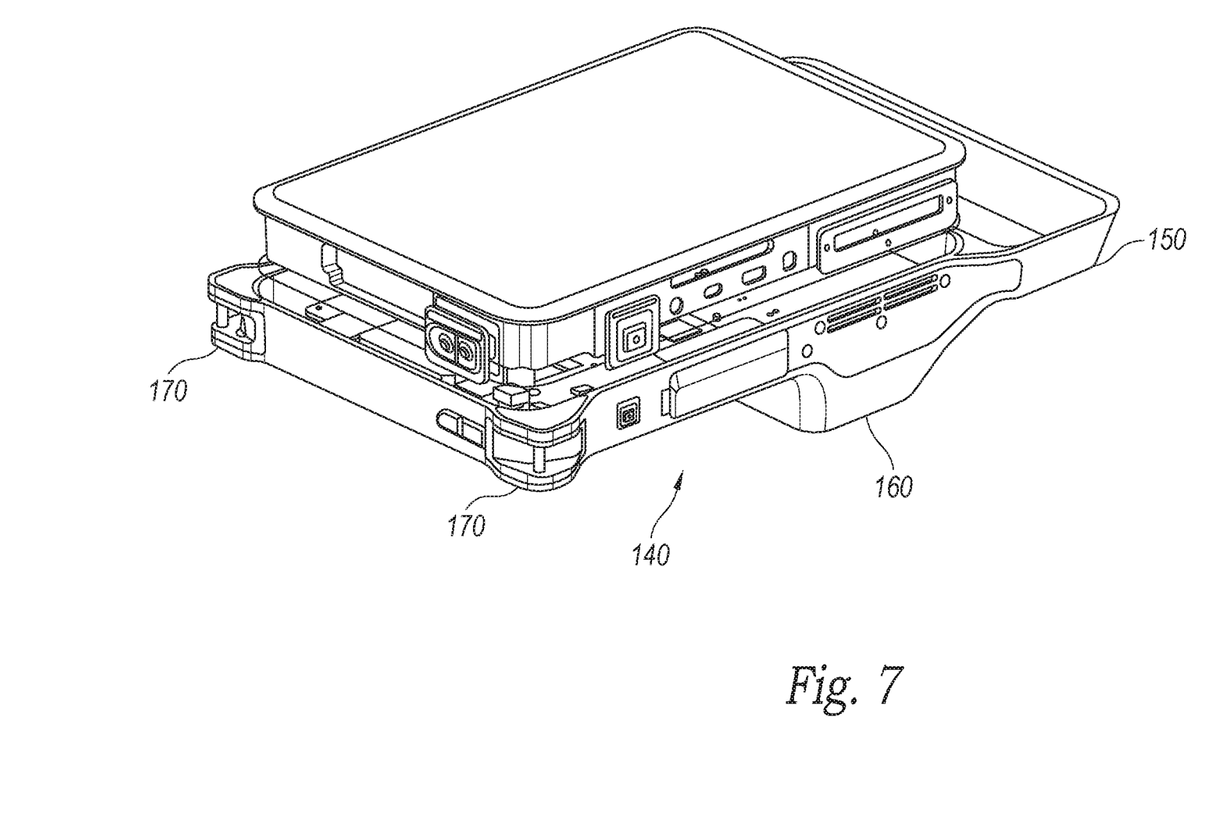
FIG. 7 illustrates an outer housing that fits around the perimeter of the thermally conductive frame in accordance with an embodiment of the disclosed technology.
Figure 8:
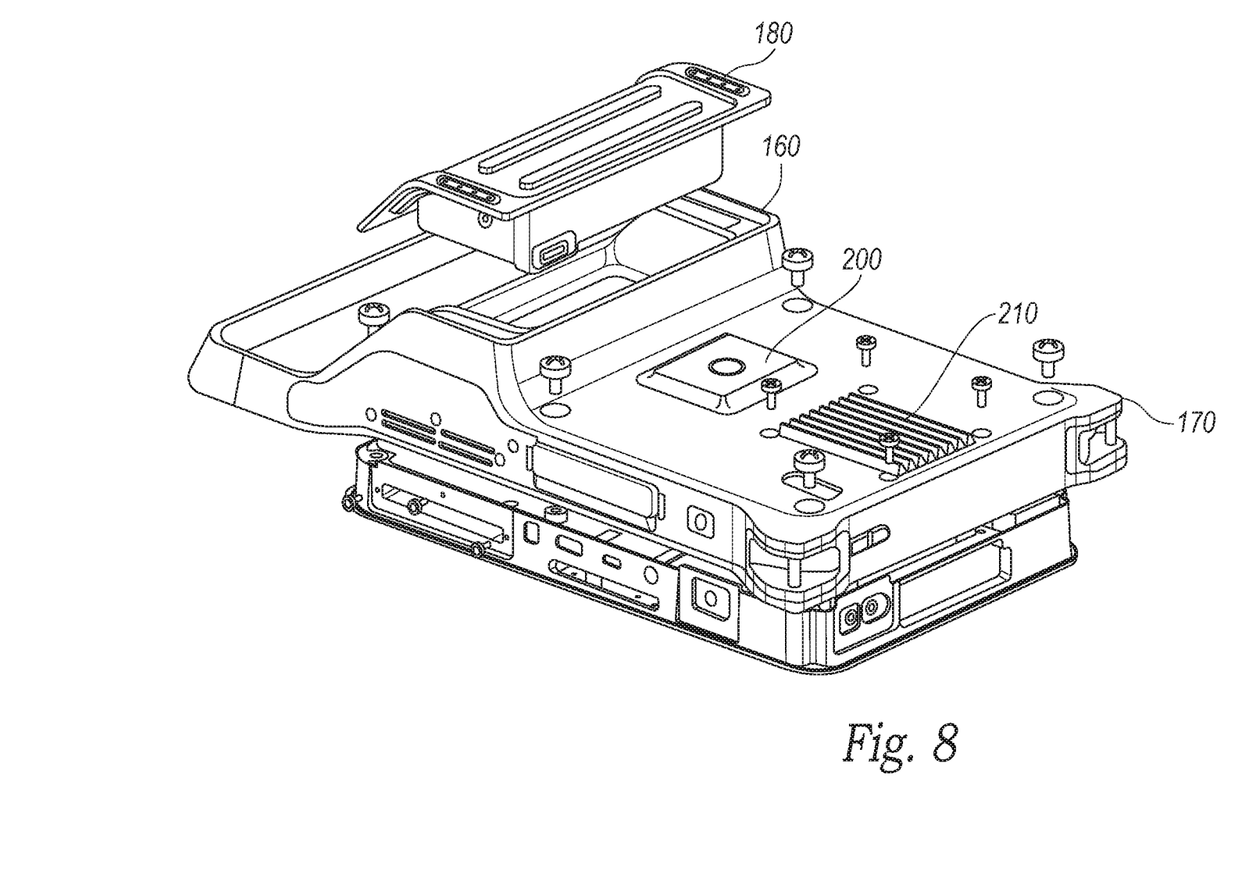
FIG. 8 shows a bottom view of the housing and a battery compartment that are secured to the thermally conductive frame in accordance with an embodiment of the disclosed technology.

FIGS. 7 and 8 show a housing 140 that is secured to thermally conductive frame 10. The housing includes a loop that is spaced from the conductive frame to define a handle 150 for the ultrasound imaging system. The housing surrounds the rim 12 of the frame 10 to protect the components in the frame and includes a battery compartment 160. In the embodiment shown, a user can grasp the handle 150 to hold the ultrasound imaging system. In addition, the user can insert their hand though the opening between the frame and the handle 150 such that their fingertips curl around a battery compartment 160 that is formed in the underside of the housing 140 in order to balance the ultrasound imaging system during hand-held use. Corner bumpers 170 in the housing 140 protect the corners of the frame 10 from potential damage if the unit is dropped on its edge. In addition, in the embodiment shown, the corner bumpers 170 include posts or pins to which a neck strap (not shown) can be clipped so that a user can carry the ultrasound imaging system around their neck or over their shoulder. One or more gaskets are positioned between the housing and the frame and between the apertures in the frame 10 and corresponding apertures in the housing 140 to prevent liquid or contaminants from getting in between any space between the housing 140 and the frame 10. The gaskets around the input/output air ports make a seal and hence isolate the plenum area from the electronics area to prevent the ingress of air, dust or water or other contaminants. This makes the unit environmentally sealed or ingress protected and still allows heat transfer with the help of active cooling.

FIG. 8 shows a bottom view of the housing 140 with a battery back 180 removed from the battery compartment 160. Batteries are replaceable and/or rechargeable so the ultrasound imaging system can be operated without a constant source of electrical power. The batteries themselves include a seal such that when they are inserted, they form an environmental seal around the housing and hence prevent air, dust or water to enter the unit. Also shown, the back side of the housing 140 includes a threaded mounting hole 200 that allows the ultrasound imaging system to be secured to a tripod or other support. A grill 210 covers the intake to the cooling fan described above to prevent access to the blades of the fan 90.

Although the disclosed technology has been described with respect to the preferred embodiments, it will be appreciated that changes can be made without departing from the scope of the invention. For example, although one fan is shown in the described embodiment, there could be more than one fan to provide the active cooling by moving air through the plenum. Therefore, the scope of the invention is to be determined by the following claims and equivalents thereof.

I claim:

1. An ultrasound imaging system, comprising:
  a frame made from a heat conductive material, the frame including:
    a bottom portion and a top portion that include with an interior surface and an exterior surface of the frame; and
    a plenum between the bottom portion and the top portion on the interior surface of the frame that includes an input port and one or more output ports;
  a fan secured to the frame that is configured to move air through the plenum of the frame from the input port to the one or more output ports, wherein the plenum has a first portion at the input port adjacent to the fan and a second portion at the one or more output ports, wherein the first portion has a first width, and the second portion has a second width that is greater than the first width; and
  a circuitry that is outside of the plenum and thermally coupled to the exterior surface of the frame via the heat conductive material, wherein heat generated outside of the plenum by the circuitry is transferred through the exterior surface into the plenum for removal by the air flowing through the plenum, the plenum being environmentally sealed to keep contaminants from coming into contact with the circuitry when the air is flowing through the plenum.

2. The ultrasound imaging system of claim 1, wherein the plenum includes cooling fins on the interior surface.

3. The ultrasound imaging system of claim 1, wherein the top portion comprises a recess to receive a cover to seal the plenum.

4. The ultrasound imaging system of claim 1, wherein the one or more output ports include two output ports exiting on opposite sides of the frame.

5. The ultrasound imaging system of claim 1, further comprising a housing surrounding the frame.

6. The ultrasound imaging system of claim 1, wherein the circuitry includes a display positioned adjacent to the exterior surface of the top portion of the frame.

7. The ultrasound imaging system of claim 1, wherein the first portion includes a funnel area that channels the air from the input port adjacent to the fan to the one or more output ports, wherein the circuitry includes first circuit elements and second circuit elements, the first circuit elements drawing more power than ether second circuit elements, one or more of the first circuit elements being located closer to the funnel area than the second circuit elements.

8. The ultrasound imaging system of claim 1, wherein the air flows in a unilateral direction in the plenum.

9. The ultrasound imaging system of claim 2, wherein the circuitry includes circuit elements that draw more power than other circuit elements of the circuitry and one or more of the circuit elements that draw more power are placed adjacent to the cooling fins.

10. The ultrasound imaging system of claim 1, wherein the plenum and the fan are configured to limit a temperature rise in the heat conductive material of the frame to a maximum temperature.

11. The ultrasound imaging system of claim 1, wherein the frame includes a first sidewall and a second sidewall that is opposite to the first sidewall, and wherein the one or more output ports include a first output port on the first sidewall and a second output port on the second sidewall.

12. The ultrasound imaging system of claim 1, further comprising a cover on the top portion to seal the plenum, wherein the top portion comprises a sidewall that extends along a perimeter of the bottom portion, and wherein the circuitry is on the exterior surface of the bottom of the frame.

13. The ultrasound imaging system of claim 1, wherein the second width is greater than the first width so that the air moves faster in the first portion than in the second portion of the plenum.

14. An ultrasound imaging system including:
  a frame having a display and a circuitry mounted thereon that are sealed with the frame so that the ultrasound imaging system is environmentally sealed;
  one or more fans to provide active cooling for the ultrasound system; and
  a chamber within the frame through which air moved by the one or more fans is passed, wherein the chamber includes external surfaces that are thermally coupled to the display and the circuitry that are outside the chamber and an interior portion of the chamber is environmentally sealed to keep contaminants flowing through the chamber from coming into contact with the circuitry and the display, wherein heat generated by the display and circuitry outside of the interior portion of the chamber is transferred through the external surfaces into the interior portion of the chamber for removal by the air moved through the interior portion of the chamber, wherein the chamber includes an input port adjacent to the one or more fans and one or more output ports, a first portion at the input port and a second portion at the one or more output ports, wherein the first portion has a first width, and the second portion has a second width that is greater than the first width.

15. The ultrasound imaging system of claim 14, the frame is made of a thermally conductive material and the chamber is defined by an enclosed space within the thermally conductive frame that is sealed except for the input port and the one or more output ports to allow the air to be moved through the chamber.

16. The ultrasound imaging system of claim 15, wherein the one or more output ports include two output ports exiting on opposite sides of the frame.

17. The ultrasound imaging system of claim 14, wherein the display is positioned adjacent to an exterior upper surface of the chamber.

18. The ultrasound imaging system of claim 14, wherein the first portion of the chamber includes a funnel area that channels air from the input port to the one or more output ports.

19. The ultrasound imaging system of claim 14, wherein the one or more fans are ingress protected.

20. The ultrasound imaging system of claim 14, wherein the chamber and the one or more fans are configured to limit a temperature rise in the frame to a maximum temperature.

* * * * *